United States Patent [19]

Williams

[11] 4,338,930
[45] Jul. 13, 1982

[54] AIRWAY INTUBATOR

[76] Inventor: R. Tudor Williams, 3423 Utah Crescent, Calgary, Alta. T2N 4A9, Canada

[21] Appl. No.: 184,612

[22] Filed: Sep. 8, 1980

[51] Int. Cl.³ ............................................. A61M 25/02
[52] U.S. Cl. ........................... 128/200.26; 128/207.14
[58] Field of Search ...................... 128/200.26, 207.14, 128/207.15, DIG. 26

[56] References Cited

U.S. PATENT DOCUMENTS

| 507,813 | 10/1893 | Hartstein | 128/207.14 |
| 3,908,665 | 9/1975 | Moses | 128/207.14 |
| 4,054,135 | 10/1977 | Berman | 128/207.14 |

FOREIGN PATENT DOCUMENTS

| 146305 | 2/1936 | Austria | 128/200.26 |
| 574736 | 4/1959 | Canada | 128/207.14 |
| 615665 | 3/1961 | Canada | 128/203.14 |
| 841990 | 5/1970 | Canada | 128/207.14 |
| 971457 | 7/1975 | Canada | 128/207.15 |
| 1032848 | 6/1978 | Canada | 128/207.15 |
| 1072414 | 2/1980 | Canada | 128/207.15 |
| 125754 | 4/1919 | United Kingdom | 128/200.26 |

Primary Examiner—Henry J. Recla
Attorney, Agent, or Firm—Beveridge, DeGrandi & Kline

[57] ABSTRACT

This invention relates to an oro-pharyngeal airway of generally ellipsoidal cross-sectional shape adapted to function as a guide and passageway for an endotracheal tube for intubation of a human larynx having distal and proximal halves and ends in which the proximal end is generally in the shape of a cylindrical tunnel of a size sufficient to accommodate a complementary endotracheal tube and in which the distal half and end is open along its lingual surface so as to permit the passage therethrough of the aforesaid complementary endotracheal tube.

4 Claims, 5 Drawing Figures

AIRWAY INTUBATOR

My invention relates to a modified airway device adapted to function especially as a guide and passageway for an endotracheal tube for intubation of a human larynx and trachea and includes the combination of a modified airway tube and endotracheal tube.

In surgery as well as in situations where paramedical personnel are involved, it becomes necessary from time to time to introduce an endotracheal tube into a patient to intubate the trachea and thus permit the passage of air into and out of the lungs of the patient and thus aid in or permit respiration.

When a patient is unconscious, the practice has been to employ a laryngoscope to aid in the placing of the endotracheal tube. A laryngoscope is, however, a difficult instrument to handle and even skilled anaesthetists very occasionally have difficulty placing an endotracheal tube with the aid of a laryngoscope and damage to the upper incisors of the patient is a not uncommon occurrence.

Furthermore, laryngoscopes are expensive, contain electrical parts and are not easily carried around.

Where the use of a laryngoscope has not proved practical or is not available, anaesthetists and medical personnel sometimes have resorted to blind nasal intubation, however, this often results in damage to the lining of the nasal passages and attendant bleeding. Also, once the endotracheal tube passes out of the nasal cavity into the pharynx, the tube is free to move laterally and difficulty may be encountered in directing the tip of the tube into the larynx and trachea.

As an aid in respiration, a standard oro-pharyngeal airway may be placed orally into the patient, however, respiratory problems may still occur due to obstructions such as the patient's tongue. Therefore a tube passing down to just above the vocal cords or, better still, into the trachea is helpful in preventing many deaths due to respiratory obstructions.

A tube by itself is not advisable since blind oral intubation is almost impossible to perform. There is also the attendant risk that the patient, by clenching his or her teeth, may kink the tube, thereby shutting off the supply of oxygen to his or her lungs.

It would, therefore, be desirable to employ a device such as an oro-pharyngeal airway as a means of assisting in the oral placement of the endotracheal tube. Due to the design of such airways, in particular their ellipsoidal cross-sectional shape, it has hitherto not been possible to employ such an airway with an endotracheal tube having a circular cross-sectional shape.

Attempts have been made in the past to design an oro-pharyngeal airway which will accomplish this purpose. It appears that in the 1930's an oro-pharyngeal airway, circular in cross-section and made of light metal in two halves which were held together with locking pins, was used for a period of time. An endotracheal tube was then passed through the airway into the glottis. The device does not appear to have been successful owing in part to the difficulty in inserting into and maintaining in the patient's pharynx, an airway of circular cross-section.

A further attempt appears to have been made in 1977 when a new version of the 1930's oro-pharyngeal divided airway was produced in plastic. While this airway was available in three sizes, it was still rounded in cross-section to accommodate the endotracheal tube and bulky, and has not met with much success.

I have avoided the problems of the earlier attempts to use oro-pharyngeal airway for blind endotracheal intubation by generally maintaining the ellipsoidal cross-sectional shape of the conventional oro-pharyngeal airway and modifying the proximal end of the airway into the shape of a cylindrical tunnel of various sizes, so as to allow the entry therein of various sized endotracheal tubes and by opening the distal half of the airway along its lingual surface so as to permit the passage therethrough of the different sizes of endotracheal tubes without changing the shape or size of the airway. By opening the distal half of the airway it has for the first time to my knowledge been possible to adapt an airway to accommodate an endotracheal tube without enlarging the size of the distal half of the airway, thus avoiding the problems of the earlier devices. This opening also allows for the passage of endotracheal tubes with different radii of curvatures and even ones with a controllable tip.

My invention therefore in one aspect relates to an improved oro-pharyngeal airway of generally ellipsoidal cross-sectional shape adapted to function as a guide and passageway for an endotracheal tube for intubation of a human larynx, having distal and proximal halves and ends in which the proximal end is generally in the shape of a cylindrical tunnel of a size sufficient to accommodate a complementary endotracheal tube and in which the distal half and end is open along its lingual surface so as to permit the passage therethrough of the aforesaid complementary endotracheal tube.

My modified airway is simple, inexpensive and can easily be carried in a physician's handbag or a paramedical person's emergency kit. Furthermore, the proximal half of the airway serves as a splint to direct the endotracheal tube into the patient's throat and over the tongue while the distal half directs the tube through the pharynx and towards the larynx and trachea.

A preferred embodiment of my invention is illustrated in the accompanying drawings and described hereafter, in which.

Figure 1:
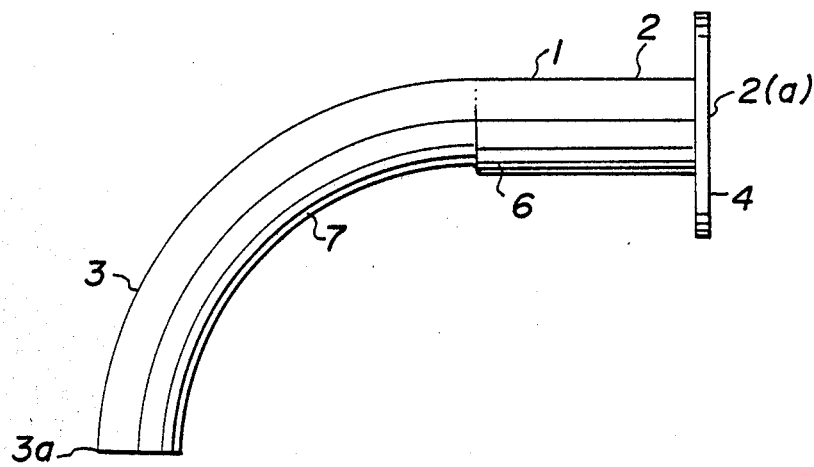
FIG. 1 is a side view of the new oro-pharyngeal airway.

Referring to FIG. 1 of the drawings, an oro-pharyngeal airway 1 that is adapted to be inserted orally into the patient's mouth, has an outer or proximal half 2 and end 2(a) for connection to breathing apparatus such as a respirator (not shown) for applying intermittent positive pressure respiration. The distal or inner half 3 of the airway 1 is inserted orally into the patient's mouth, over the tongue and into the pharynx. The flange 4 on the proximal end 2(a) of the airway 1 rests against the outer surface of the lips or teeth of the patient to prevent the airway 1 from passing completely into the patient's mouth.

Figure 2:
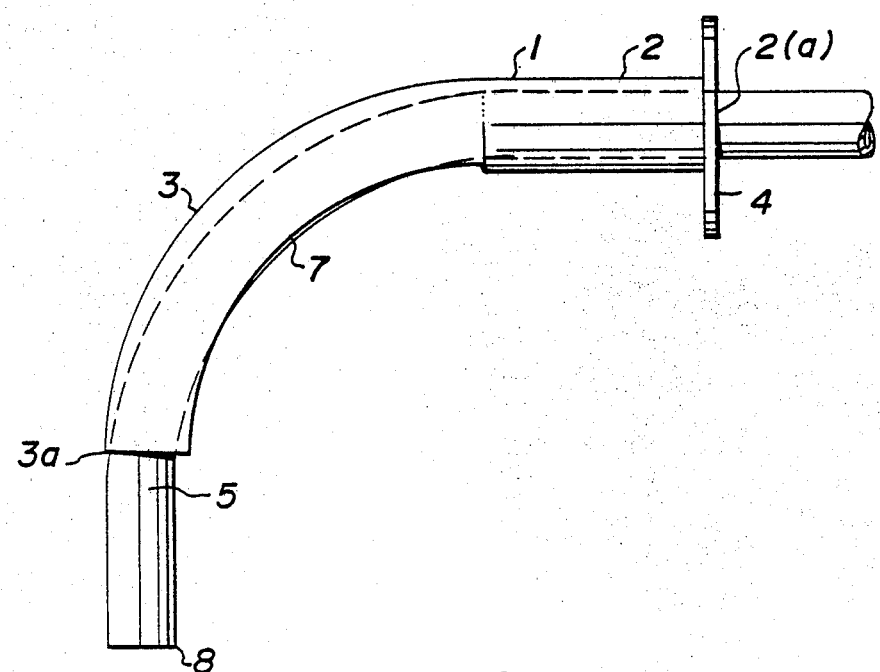
FIG. 2 is a side view of the oro-pharyngeal airway with the complementary endotracheal tube in place.
Figure 4:
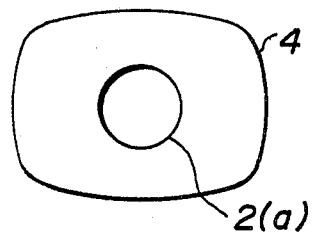
FIG. 4 is a view of the proximal end of the airway.

From FIGS. 2 and 4 it will be seen that the outer proximal half 2 of the airway 1 has an interior cylindrical shape of a diameter sufficient to accommodate a complementary endotracheal tube 5. Depending upon whether the device is intended to be used for children or adults, the airway 1 and the tube 5 will be sized accordingly.

Figure 3:
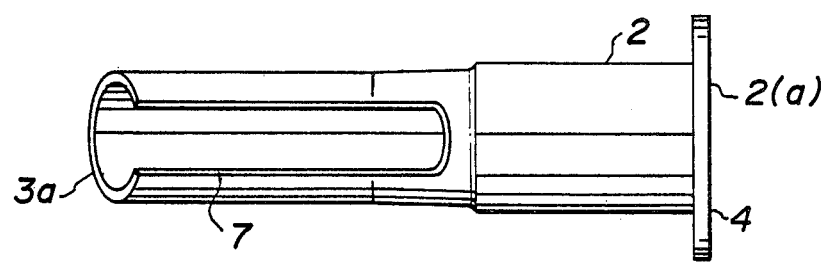
FIG. 3 is a view of the lingual surface of the airway.

As can be seen in FIGS. 1, 2 and 3 of the drawings, the distal half 3 and end 3(a) of the airway 1 has the conventional ellipsoidal cross-sectional shape of a standard airway, however, the lingual or lower side 6 of the distal half 3 and end 3(a) is open to accommodate the endotracheal tube 5.

The airway, with the tube 5 inserted therein at least to the distal end 3(a), may be inserted into the patient's mouth even while the patient is unconscious, without risking damage to the patient's teeth, following which the endotracheal tube 5 can be passed through the airway 1 and into the patient's trachea with ease. Furthermore, the risk that the tube 5 will be accidentally inserted into the patient's esophagus is substantially lessened. The opening 7 on the lingual side 6 of the distal end 3(a) of the airway 1 also permits some manipulation of the tip 8 of the endotracheal tube 5. Even if the tip 8 is not advanced into the patient's trachea, respiratory obstruction is less likely to occur than with an ordinary airway as the location of the tube 5 can be adjusted to allow a free flow of air. The airway 1 will allow the placing of the tube 5 separately following placing of the airway 1. With the airway 1 in place, the tube 5 can be removed from or replaced into the patient's trachea with ease.

Figure 5:
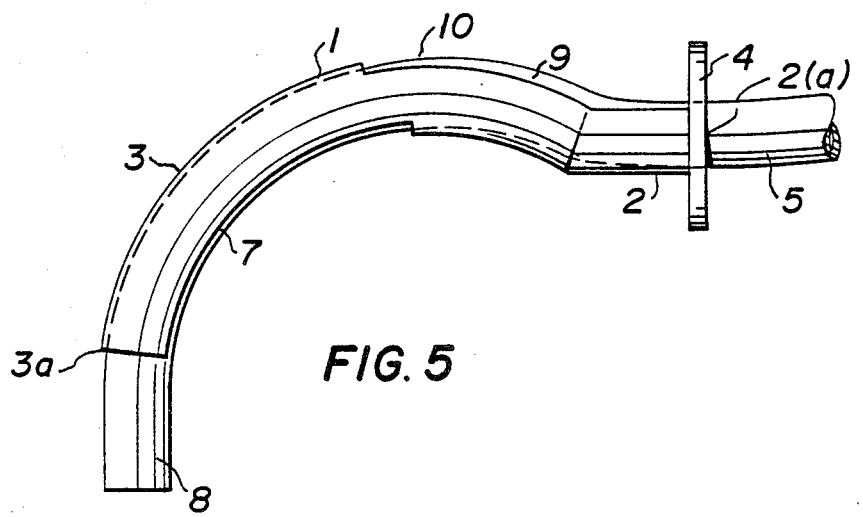
FIG. 5 is a side view of an alternative embodiment of the airway invention.

If desired, the airway 1 may be modified slightly and still accomplish the desired result. For example, although less desirable, the cylindrical shape of the proximal end of the airway may be of the same cross-sectional shape as a standard airway but enlarged so as to accomodate the outside diameter of the endotracheal tube 5. Alternatively, a portion of the superior surface of the proximal end of the airway may be removed to permit the passage of the tube 5 through the proximal end of the airway and towards the distal end thereof. Such a construction is shown in FIG. 5 in which there is an opening 9 on the superior side 10 of the proximal end 2(a) of the airway 1 and an opening 7 on the lingual side 6 of the distal end 3(a) of the airway 1. The endotracheal tube 5 is shown inserted into the airway 1 with its distal end 8 extending slightly from the distal end 3a of the airway 1.

Other modifications to the oro-pharyngeal airway to accomplish the same result may be possible without departing from the purpose and intent of the invention, however, I believe that the modified airway disclosed in FIGS. 1 to 4 and described herein is the preferred embodiment of my invention.

I claim:

1. An improved oro-pharyngeal airway adapted to function as a guide and passageway for an endotracheal tube for intubation of a human larynx, said airway having distal and proximal halves and ends of generally ellipsoidal, exterior cross-sectional shape, in which the airway has an air passage therethrough of a size sufficient to accommodate a complementary endotracheal tube and in which the distal half and end is open along its lingual surface so as to permit the passage therethrough of the aforesaid complementary endotracheal tube.

2. An oro-pharyngeal airway as described in claim 1, in which the proximal end of the airway is open along its superior surface.

3. An oro-pharyngeal airway as described in claims 1 or 2, in which the proximal end has an interior shape of generally circular cross-section.

4. An oro-pharyngeal airway as described in claims 1 or 2, in which the proximal end has an interior shape of generally ellipsoidal cross-section.

* * * * *